United States Patent [19]
Jones et al.

[11] Patent Number: 6,123,959
[45] Date of Patent: Sep. 26, 2000

[54] AQUEOUS COMPOSITION COMPRISING ACTIVE INGREDIENTS FOR THE DE-PIGMENTATION OF THE SKIN

[75] Inventors: Kenneth Jones, Broomfield; Abeysinghe Padmapriya, Boulder, both of Colo.; Ernst E. Teichmüller, Schlüchtern; Gabriele Blume, Strasse, both of Germany

[73] Assignee: Univera Pharmaceuticals, Inc., Broomfield, Colo.

[21] Appl. No.: 09/066,161

[22] Filed: Apr. 24, 1998

[51] Int. Cl.$^7$ .............................. A61K 9/127; A61K 7/00
[52] U.S. Cl. ................................. 424/450; 424/62
[58] Field of Search ...................... 424/450, 62; 514/453, 514/456

[56] References Cited

U.S. PATENT DOCUMENTS 5,279,834    1/1994    Meybeck .................................. 424/450

OTHER PUBLICATIONS

Holdsworth (1972) *Chromones in Aloe Species, Part I*—*Aloesin*, PM 19(4):322.
Holdsworth (1972) *Chromones in Aloe Species, Part II*—*Aloesone*, PM 22(1):54.
Lee and Kim (1995) Cosmetics and Toiletries 110:51–56.
Yagi et al. (1987) Planta Medica 515.
Hirata and Suga (1977) 32c:731–734, Biologically Active Constituents of Leaves and Roots of *Aloe arborescens* var. *natalensis*.
Gombert (1997) Cosmetics and Toiletries Manufacture Worldwide, pp. 151–157.

*Primary Examiner*—Gollamudi S. Kishore
*Attorney, Agent, or Firm*—Swanson & Bratschun LLC

[57] ABSTRACT

The present invention discloses aqueous compositions comprising liposomes of phospholipids, and at least one competitive inhibitor of an enzyme for the synthesis of melanin, in combination with at least one non-competitive inhibitor of an enzyme for the synthesis of melanin. The invention also includes the use of the compositions of this invention for the de-pigmentation of skin.

15 Claims, No Drawings

AQUEOUS COMPOSITION COMPRISING ACTIVE INGREDIENTS FOR THE DE-PIGMENTATION OF THE SKIN

FIELD OF INVENTION

The present invention relates to an aqueous liposome composition containing active ingredients which inhibit tyrosinase, an enzyme involved in the synthesis of melanin, and the use of this composition for the de-pigmentation (whitening) of the skin.

BACKGROUND OF THE INVENTION

There is a world-wide demand for products able to inhibit or prevent excessive pigmentation of the skin. In Europe these products tend to be used to treat age and liver spots or freckles, whereas in Asia they are used to achieve the beauty ideal of a white, flawless skin.

Melanin, the skin's natural pigment, is synthesized in the melanocytes in varying concentrations, depending on skin type (genetic disposition) and environmental effects. Melanocytes are cells which occur in the basal membrane of the epidermis, and account for between 5% and 10% of the cellular content (approximately 1200–1500 melanocytes per $cm^2$). Ultraviolet (UV) light stimulates the cells in the basal layer, causing them to divide more rapidly. Melanocytes are also stimulated by UV light, producing greater quantities of melanin. The melanin is then transported into the keratinocytes, where it becomes visible as a brown skin color.

The number of melanocytes in human skin is more or less the same, irrespective of skin color. The color of the skin is largely dependent on the quantity and type of melanin produced (black eumelanin or yellow to reddish-brown pheomelanin). Asians and light-skinned people have lower levels of eumelanin than dark-skinned people, and correspondingly less protection against the effects of radiation.

People with red hair are characterized by pigmentation with pheomelanin, and have little or no photo-protection. Additionally, the distribution of melanin in the skin also varies. In people with light skin, the greater part of the pigment lies in the basal layer, whereas in those with dark skin, the melanin is spread throughout, reaching into the horny layer.

An enzyme works as a catalyst to convert a substrate into a product. During the competitive inhibition of an enzyme by a substance with a low molecular weight, the substance forces the actual substrate of the enzyme out of the catalytic domain, so that the substrate can no longer be converted with the help of the enzyme. During non-competitive inhibition, the inhibitor interacts directly with the enzyme, though at a different point than that required for the conversion of the substrate. The combination of a competitive and non-competitive inhibitor is particularly advantageous due to the fact that competitive and non-competitive inhibition have different working mechanisms, which means that the inhibitors can, independently of one another, each have its own effect on one and the same enzyme. One effect can support the other, although this is not necessarily the case. A skilled person can easily differentiate between a competitive and a non-competitive inhibitor by means of common biochemical measuring methods, for example by using the Lineweaver Burk diagram.

Tyrosinase is the key enzyme in the synthesis of melanin. It is activated when exposed to UV light, and intervenes inductively in several intermediate stages of pigment formation as illustrated in Scheme 1. It has been determined that tyrosinase needs both the substrate and divalent metal ions for its catalytic activity. The processes presently used for inhibiting the synthesis of melanin with a view to lightening skin are based on substances which interact directly with the tyrosinase, or indirectly regulate its activity, e.g., by complexing the necessary metal ions.

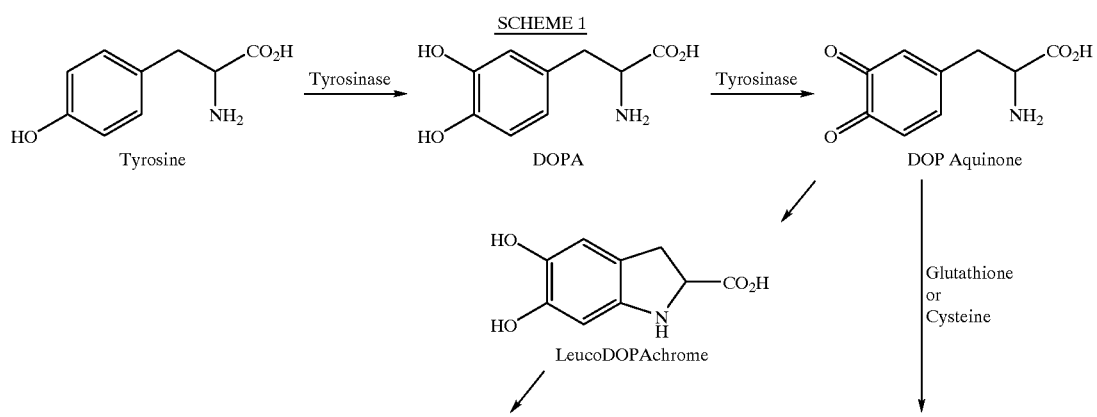

SCHEME 1

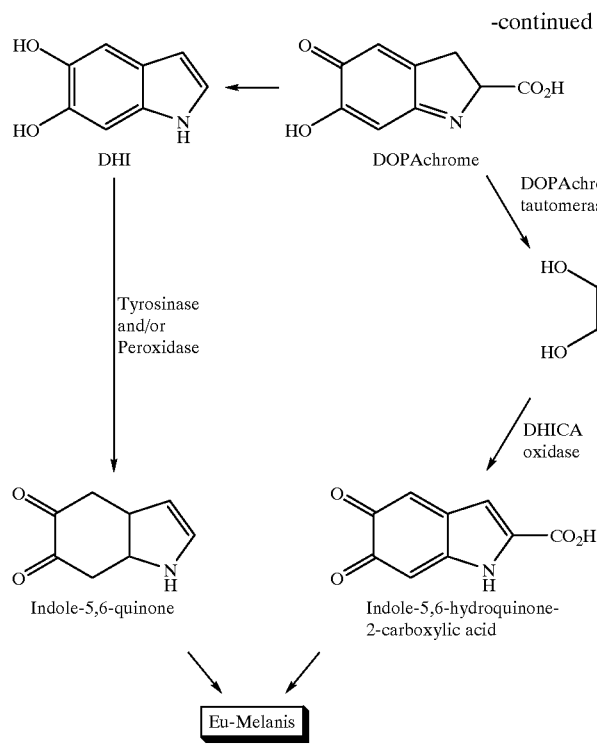
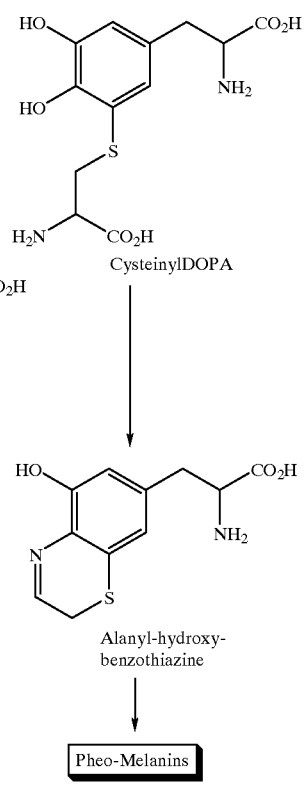

-continued

To date, the best-known active substance for de-pigmentation is hydroquinone. If applied over long periods of time, however, hydroquinone can have serious side effects, which has led to its being permitted only in limited concentrations in some countries, and to its being completely forbidden for applications in cosmetic products in other countries. Furthermore, hydroquinone leads to permanent de-pigmentation, and thus to increased photosensitivity of the skin when exposed to UV light.

Better tolerated skin lightening substances currently being used are of natural origin, e.g., arbutin (from the leaves of the common bearberry, Uvae ursi), liquorice extract (from liquorice root), ascorbic acid (vitamin C from citrus fruits) and their derivatives, as well as kojic acid (from carbohydrate solutions under the effect of certain bacteria). These substances, which are highly soluble in water, act on the tyrosinase as competitive inhibitors; however, they are unstable in some formulations, and have the disadvantage that only very small quantities penetrate the deeper skin layers and reach the melanocytes in the basal membrane. A further disadvantage of these substances is their low level of efficacy, which necessitates their being used in high concentrations. Compared to the quantity of hydroquinone used, 17 times as much ascorbic acid and over 100 times as much arbutin is required to achieve a similar effect.

Gombert describes two cosmetic products for lightening skin, both of which are produced from plants. (Gombert (1997) Cosmetics and Toiletries Manufacture Worldwide, pp.151–157). Both products contain a mixture of several competitive tyrosinase inhibitors in an aqueous solution, emulsified into creams. An in vitro enzyme test was carried out, in which it was possible to show that the substances used had an efficient inhibitory effect; however with in vivo tests, it was not until a cream with a 10% active ingredient content had been applied for at least 42 days that a demonstrable de-pigmentation of the skin occurred. In one test involving 10 people using a cream with a 3% active ingredient content, proof of any positive effect at all could only be found with two people. The author specifically points out that, since the natural substances used in the formulation are extremely unstable, strong antioxidants must be added to the formulation. Also, if the finished formulations are stored at temperatures below 15° C., the substances can crystallize.

Lee and Kim (Cosmetics and Toiletries 110:51–56, October 1995), describe a substance isolated from the bark of the roots of the mulberry bush Broussonetia papyrifera, which acts as a free radical scavenger. As the formation of melanin, referred to as melanogenesis, is increased by the presence of free radicals in the skin, it can be reduced with the help of a free radical scavenger of this type. The subject of this article is not the de-pigmentation of skin, but rather the suppression of melanogenesis with the help of a free radical scavenger. Furthermore, it takes over 40 days for the described effect to occur. Here, too, attention is drawn specifically to the instability of the active substances in the formulation.

Aloe is an intricate plant which contains many biologically active substances. (Cohen et al. in Wound Healing/ Biochemical and Clinical Aspects, 1st ed. W B Saunders, Philadelphia (1992)). Over 300 species of Aloe are known, most of which are indigenous to Africa. Studies have shown that the biologically active substances are located in three separate sections of the aloe leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, Aloe products have been used in dermatological applications for the treatment of burns, sores and other wounds. These uses have stimulated a great deal of research in identifying compounds from Aloe plants that have clinical activity, especially anti-inflammatory activity. (See, e.g., Grindlay and Reynolds (1986) J. of Ethnopharmacology 16:117–151; Hart et al. (1988) J. of Ethnopharmacology 23:61–71). As a result of these studies there have been numerous reports of Aloe compounds having diverse biological activities, including anti-tumor activity, anti-gastric ulcer, anti-diabetic, anti-tyrosinase activity (see, e.g., Yagi et al. (1977) Z. Naturforsch 32c:731–734) and antioxidant activity (see, International Application Serial No. PCT/US95/07404).

Yagi et al. disclose a group of compounds isolated from Aloe, particularly aloesin and one of its derivatives, 2"-O-feruloylaloesin, which are effective inhibitors of tyrosinase. (Yagi et al. (1987) Plant Medica 515–517). Biochemical testing of the enzyme inhibition by means of the Lineweaver Burk diagram showed that these substances are non-competitive inhibitors of tyrosinase. There is no disclosure of the inhibitors being applied in in vivo tests.

It is the object of the present invention to provide a skin-compatible composition which results in rapid, safe, effective and reversible de-pigmentation of the skin when applied externally.

SUMMARY OF THE INVENTION

The present invention includes aqueous compositions comprising liposomes of phospholipids, and at least one competitive inhibitor of an enzyme for the synthesis of melanin, in combination with at least one non-competitive inhibitor of an enzyme for the synthesis of melanin. Encapsulation of the inhibitors into a liposome both improves the bioavailability of the inhibitors and stabilizes the compounds, which tend to hydrolyze in aqueous solutions.

In a preferred embodiment the compositions of the present invention are selected to inhibit the enzyme tyrosinase. The inhibition of tyrosinase is particularly advantageous as tyrosinase is one of the key enzymes in the metabolism of melanin. Thus, it follows that not only the initial stage of melanin synthesis is inhibited, but other intermediate stages of melanin metabolism are also regulated.

In the most preferred embodiment of this invention the competitive inhibitor is arbutin and the non-competitive inhibitor is aloesin or a derivative thereof. It has been discovered that when arbutin is used in combination with aloesin or a derivative thereof the inhibitory effects of the two substances are additive.

In a preferred embodiment of the present invention the inhibitors formulated in the composition are of plant origin, as this brings about the desirable and pleasant result of excellent skin compatibility.

The invention also includes the use of the compositions of this invention for the de-pigmentation of the skin.

It is to be understood that both the foregoing general description and the following detailed description are exemplary and explanatory only and are not restrictive of the invention as claimed.

DETAILED DESCRIPTION OF THE INVENTION

The present invention discloses aqueous compositions comprising liposomes of phospholipids, and at least one competitive inhibitor of an enzyme for the synthesis of melanin in combination with at least one non-competitive inhibitor of an enzyme for the synthesis of melanin. In a preferred embodiment the compositions of the present invention are selected to inhibit the enzyme tyrosinase, one of the key enzymes in the metabolism of melanin. This invention also includes the use of the compositions of this invention for the de-pigmentation of the skin.

The compositions of the present invention can also contain one or more additional active substances for de-pigmentation which act independently of the other active substances contained in the composition.

Certain terms used to describe the invention herein are defined as follows:

As used herein a "competitive inhibitor" refers to a substance which prevents the action of an enzyme involved in the synthesis of melanin by reversibly interacting with the active site of the enzyme. A competitive inhibitor thus diminishes the rate of catalysis by reducing the proportion of enzyme molecules that have bound to the substrate. In a preferred embodiment of this invention the enzyme is tyrosinase. The competitive inhibitors to tyrosinase that can be used in the composition and method of this invention include any such inhibitors known to those of skill in the art. Specifically, the competitive inhibitors that can be used in the composition and method of this invention include, but are not limited to arbutin, vitamin C and its derivatives, kojic acid, glutathion, liquorice extract and mulberry tree extract.

In a preferred embodiment the competitive inhibitor is arbutin, which as discussed below, has been shown to have an additive inhibitory effect when used in combination with aloesin or a derivative thereof.

A "non-competitive inhibitor" refers to a substance which binds to a site other than the active site of the enzyme. Thus, an enzyme and a non-competitive inhibitor can simultaneously bind to the substrate. A non-competitive inhibitor acts by decreasing the turnover number of an enzyme.

The non-competitive inhibitors of this invention include aloesin which has the following chemical structure:

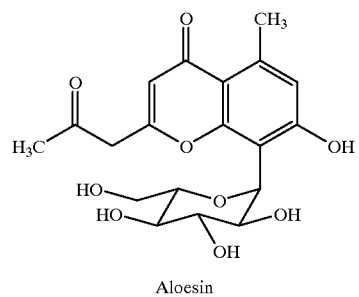

Aloesin and derivatives thereof selected from compounds having the following chemical structures:

I

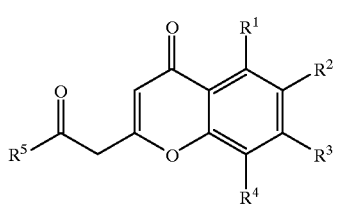

wherein $R^1$, $R^2$, $R^3$, $R^4$ and $R^5$ are independently selected from the group consisting of H, alkyl, alkoxy, acyl, acyloxy, acylamino and polyalcohols or derivatives thereof including, but not limited to sugar derivatives, wherein said alkyl, alkoxy, acyl, acyloxy, acylamino and polyalcohol groups and derivatives thereof can be saturated or unsaturated and have between 1 and 20 carbon atoms;

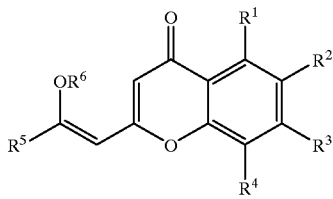

II wherein $R^1$, $R^2$, $R^3$, $R^4$, $R^5$ and $R^6$ are independently selected from the group consisting of H, alkyl, alkoxy, acyl, acyloxy, acylamino and polyalcohols or derivatives thereof including, but not limited to sugar derivatives, wherein said alkyl, alkoxy, acyl, acyloxy, acylamino and polyalcohol groups and derivatives thereof can be saturated or unsaturated and have between 1 and 20 carbon atoms;

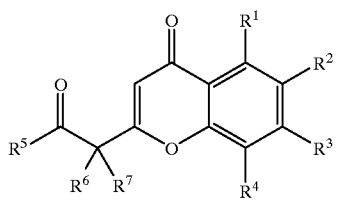

III wherein $R^1$, $R^2$, $R^3$, $R^4$, $R^5$, $R^6$ and $R^7$ are independently selected from the group consisting of H, alkyl, alkoxy, acyl, acyloxy, acylamino and polyalcohols or derivatives thereof including, but not limited to sugar derivatives, wherein said alkyl, alkoxy, acyl, acyloxy, acylamino and polyalcohol groups and derivatives thereof can be saturated or unsaturated and have between 1 and 20 carbon atoms; and

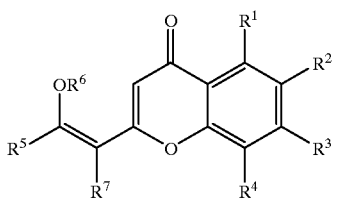

IV wherein $R^1$, $R^2$, $R^3$, $R^4$, $R^5$, $R^6$ and $R^7$ are independently selected from the group consisting of H, alkyl, alkoxy, acyl, acyloxy, acylamino and polyalcohols or derivatives thereof including, but not limited to sugar derivatives, wherein said alkyl, alkoxy, acyl, acyloxy, acylamino and polyalcohol groups and derivatives thereof can be saturated or unsaturated and have between 1 and 20 carbon atoms.

The R substituents function to stabilize the compound in the formulation, increase the efficacy of the inhibitor and improve the penetration of the compound into the skin.

In a preferred embodiment of the invention the aloesin derivative is selected from the group of compounds having the following chemical structure:

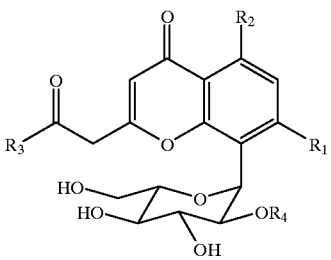

V wherein
  $R_1$, $R_2$ and $R_3$ are independently selected from the group consisting of H, OH, alkyl groups having from 1 to 20 carbon atoms, alkoxy groups having from 1 to 20 carbon atoms, acyl groups having from 1 to 20 carbon atoms, acyloxy groups having from 1 to 20 carbon atoms, acylamino groups having from 1 to 20 carbon atoms, and polyalcohol groups, wherein each of said alkyl, alkoxy, acyl, acyloxy and acylamino groups may be saturated, unsaturated and substituted; and
  $R_4$ is selected from the group consisting of aromatic substituted carboxylic acids attached to the linking oxygen via the carboxyl carbon thereby forming the ester, wherein said carboxylic acids are selected from the group consisting of, but not limited to phenylacetic acid, DOPA, tyrosine and cinnamic acid and derivatives thereof, including but not limited to ferulic acid. $R_4$ may also be the residue of kojic acid, even though this is not a carboxylic acid in the true sense (kojic acid contains no carboxyl groups).

In a preferred embodiment said acyl groups are hydroxy substituted and said acyloxy groups are derived from fatty acids and dicarboxylic acids.

In particularly preferred embodiments the non-competitive inhibitor is octylaloesin which has the following chemical structure:

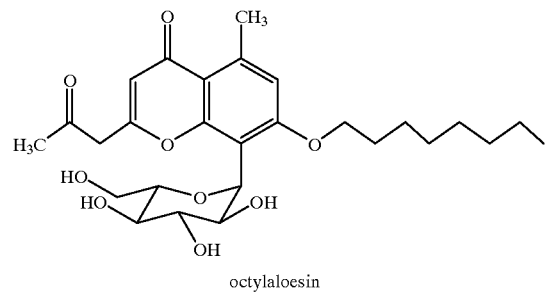

octylaloesin or 2"-O-feruloylaloesin ($R_1$=OH, $R_2$ and $R_3$=CH$_3$, $R_4$=ferulic acid in formula V above). Compared to aloesin, octylaloesin has a significantly higher inhibitory effect on tyrosinase, and thus can be used in considerably lower concentrations.

Other non-competitive inhibitors of tyrosine, which would be known to one of skill in the art may also be used in the composition according to the present invention.

"Liposomes" are spherical structures (vesicles) comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space.

The phospholipids that can be used in the composition and method of this invention include any phospholipids known to those of skill in the art to be useful for making liposomes, including but not limited to phosphoglycerides. Phosphoglycerides consist of a glyceride backbone, one or two fatty acid chains and a phosphate or phosphorylated alcohol. The major phosphoglycerides are derivatives of phosphatidate. Examples of phosphatidyl groups that can used in the compositions of this invention include, but are not limited to phosphatidyl choline, lyso-phosphatidyl choline, phosphatidic acid, phosphatidyl ethanolamine and various combinations thereof. Examples of fatty acid residues that can be used in the compositions of this invention include but are not limited to linoleic acid, oleic acid, palmitic acid and stearic acid. Hydrogenated phospholipids may also be used in the compositions of this invention. In a preferred embodiment liposomes prepared from soya phospholipids are used.

Liposomes are used to deliver drugs which are toxic in the free form and to release drugs over a prolonged period of time, reducing the frequency of administration. In addition, liposomes can also be used to form aqueous dispersions of hydrophobic or amphiphilic drugs. As the vesicles are amphiphilic in character, the encapsulated substances can select the surroundings most favorable for them. In the present invention, both the competitive inhibitor and the non-competitive inhibitor are encapsulated in liposomes. The liposomes function both to improve the bioavailability of the inhibitors to the melanocytes in the basal layer of the skin and to stabilize the inhibitors, which tend to hydrolyze in aqueous solutions. The stability of the plant skin-lightening active substances in particular, is increased up to four times through the encapsulation in the lipid vesicles. Additionally, some of the fatty acids present in the liposomes, e.g., linolenic acid, also inhibit the synthesis of melanin and thus also promote de-pigmentation. (Maeda and Fukuda (1991) J. Soc. Cosmet. Chem. 42:361–368). The vesicle size of the liposomes of this invention is between 80 to 400 nm in diameter.

In a preferred embodiment of the present invention the inhibitors are used in concentrations of about 0.05 to 7.5 percent by weight of the competitive inhibitor and 0.05 to 1.5 percent by weight of the non-competitive inhibitor based on the total weight of the composition. In the most preferred embodiment the inhibitors are used in concentrations of about 3.5 to 5.5 percent by weight of the competitive inhibitor and 0.75 to 1.25 percent by weight of the non-competitive inhibitor, based on the total weight of the composition. If a combination of arbutin with aloesin or one of its derivatives is used, then the preferred concentrations are about 3.5 to 5.5 percent by weight of arbutin and 0.75 to 1.25 percent by weight of aloesin or aloesin derivative. Particularly preferred is an aqueous composition containing approximately 4 percent by weight of arbutin and approximately 1 percent by weight of aloesin or aloesin derivative, each based on the total weight of the composition.

The phospholipid content of the aqueous composition is about 5 to 20 percent by weight, based on the total weight of the composition. In a preferred embodiment, the phospholipid content of the composition is about 8 to 12 percent by weight. In a preferred embodiment liposomes from soya phospholipids with a phosphatidyl choline content of at least 73 percent by weight are used. A phosphatidyl choline content of 73 to 79 percent by weight is especially preferred. Examples of phospholipid fractions that can be used include, but are not limited to: a) 73 to 79 percent by weight of phosphatidyl choline, 0 to 6 percent by weight of lyso-phosphatidyl choline, about 8 percent by weight of phosphatidic acid, about 4 percent by weight of phosphatidyl ethanolamine and about 9 percent by weight of other lipids; b) 90 to 96 percent by weight of phosphatidyl choline and 0 to 6 percent by weight of lyso-phosphatidyl choline; or c) a minimum of 95 percent by weight of phosphatidyl choline and a maximum of 2 percent by weight of lyso-phosphatidyl choline.

The fatty acid residues of the soya phospholipids are mainly derived from unsaturated fatty acids, with linoleic acid making up the greater part. The following is a typical fatty acid composition: 61 to 71 percent of linoleic acid, 3 to 7 percent of linolenic acid, 6 to 13 percent of oleic acid, 10 to 15 percent of palmitic acid and 1.5 to 4 percent of stearic acid.

Hydrogenated phospholipids with a phosphatidyl choline content of at least 73 percent by weight, preferably from 75 to 95 percent by weight, may also be used.

In addition to the components already mentioned, the composition according to the present invention can contain one or more alcohols in concentrations of up to 20 percent by weight, based on the total weight of the composition. Alcohols that can be used include, but are not limited to, ethanol and i-propanol. In a preferred embodiment the alcohol used is ethanol.

In addition to an alcohol, the aqueous composition of the present invention may also contain a preservative. Suitable preservatives include, but are not limited to formaldehyde, parabene and Euxyl K400°. If the preservative and alcohol are present together, the alcohol content is generally 1 to 4 percent by weight.

The pH of the composition according to the present invention generally ranges from 5 to 7.5. The physiologically ideal pH value for the skin is determined by each particular application. To adjust the pH, the composition may also contain a buffer system such as a phosphate buffer ($KH_2PO_4/Na_2HPO_4$).

The composition may also contain further auxiliary substances commonly used in the formulation of cosmetic products. These substances are known to those of skill in the art.

In the most preferred embodiment the composition of this invention contains arbutin as the competitive inhibitor, in a concentration of about 4 percent by weight and aloesin or one of its derivatives as the non-competitive inhibitor, in a concentration of about 1 percent by weight, an alcohol in a concentration of about 16 percent by weight, and phospholipids in a concentration of about 10 percent by weight, each based on the total weight of the composition.

The compositions according to the present invention can be produced by any process for the production of liposomes known in the art. (See, e.g., *Liposomes—A Practical Approach,* published by R. C. New (Oxford University Press, 1990). Aqueous compositions containing an alcohol according to one embodiment of the present invention can be produced by first dissolving the water-soluble inhibitor in distilled water and dissolving the phospholipids and any inhibitors used which are not soluble in water in some of the alcohol. The resulting lipid solution is slowly added to the aqueous solution while stirring the mixture. Liposomes encapsulating the active substances are formed spontaneously, and are broken up by the application of energy, e.g., by stirring at high speeds, by high-pressure filtration, ultrasonic treatment, extrusion or homogenization. The remaining alcohol and if necessary extra water containing a buffer system are then added, and the mixture is stirred again until the desired particle size and distribution of the liposomes (polydispersity preferably<1.0) has been reached.

Depending on the application, the composition according to the present invention may be further diluted with water before use.

The compositions of the present invention are used to de-pigment skin by applying the formulation evenly to the surface of the skin to be whitened (topical application). In this way, the composition may be used both to lighten larger skin areas, as well as for specific applications to areas of strong pigmentation, e.g., freckles, age and liver spots. In a preferred embodiment the formulation is used in creams or lotions.

Using the composition of the present invention, a much more rapid de-pigmentation of the skin (visible within 10 to 14 days) can be achieved than was possible with formulations known in the art. This is a result of the additive effect of the combination of the competitive and non-competitive inhibitors and the increased bio-availability and stability of the active substances, as a result of encapsulation in a liposome. Additionally, the de-pigmentation is reversible and does not produce any patchiness of the skin.

The additive effect of the inhibitors and the increased bio-availability of the active substances also decreases the dose level of inhibitor that is necessary to de-pigment skin to a level which will not bring about any dose-related side effects. When used alone, it is difficult for the hydrophilic active substances to penetrate the skin layer, which is why they have been included in relatively high doses in formulations previously described in the art.

Example 1 describes the preparation of an aqueous liposome dispersion containing arbutin and aloesin.

Example 2 describes an in vivo study using the composition of Example 1. This in vivo study demonstrates that a significantly higher level of de-pigmentation of the skin can be achieved after exposure to UV light following the application of liposomally encapsulated active ingredients than with the same non-encapsulated substances in aqueous solutions.

Example 3 describes an in vitro tyrosine inhibition assay using the inhibitors arbutin and aloesin, both individually and in combination. In this example the conversion of L-Dopa, a substrate of tyrosinase, into dopachrome was monitered by measurement of the absorption of light at 475 nm. This example illustrates that combinations of aloesin and arbutin have an additive effect, and thus when combined bring about greater inhibition of tyrosinase than either inhibitor individually. This is by no means an expected result, since the combination of the two working principles of competitive and non-competitive inhibition do not necessarily add to each other.

The following examples are designed to illustrate the present invention, while demonstrating the high efficacy of the composition. They are provided for illustrative purposes only and are not intended to limit the scope of the invention.

EXAMPLES

Example 1

Production of an Aqueous Liposome Dispersion Containing Arbutin and Aloesin

Table 1 summarizes the materials and amounts used for each step in the preparation an aqueous liposome dispersion containing arbutin and aloesin. Briefly, the aloesin and arbutin were dissolved in water (step A). The phospholipids were dissolved in alcohol (33 g) (step B). While being stirred (2700 r.p.m.) at 9° C. the alcoholic lipid solution from step B was dripped into the aqueous solution from step A over a period of 17 minutes. Stirring was continued under the same conditions for an additional 20 minutes. Additional alcohol, was then added (step C) and the mixture was stirred for an additional 10 minutes. A buffer solution ($KH_2PO_4$ and NaOH) prepared as set forth in step D was then added to the dispersion and the mixture was stirred for an additional 10 minutes. The pH of the liposome dispersion produced in this way was 6.83, the mean diameter of the liposomes was 158.6 nm, and the polydispersity was 0.226.

TABLE 1

Summary of the Preparation of a Liposome Dispersion Containing Arbutin and Aloesin

| Step | Amount | Material |
|---|---|---|
| A | 648.20 g | Distilled water |
|  | 10.00 g | Aloesin |
|  | 40.00 g | Arbutin |
| B | 100.00 g | Phospholipids* |
|  | 33.30 g | Ethanol (pure) |
| C | 132.00 g | Ethanol (pure) |
| D | 30.00 g | Distilled water |
|  | 5.00 g | $KH_2PO_4$ |
|  | 1.50 g | Aqueous NaOH solution (30%) |
|  | 1000.00 g |  |

*Phospholipid fraction (available from Nattermann, Germany):
    phosphatidyl choline    (73–76 percent by weight)
    lyso-phosphatidyl choline    (0–6 percent by weight)
    phosphatidic acid    (<8 percent by weight)
    phosphatidyl ethanolamine    (<4 percent by weight)
    other lipids    (approx. 9 percent by weight)
    (percentages are based on dry substance)

Example 2

In Vivo Testing of Skin De-pigmentation by the Composition of Example 1

The composition from Example 1 was tested at two different concentrations: undiluted (100%) and diluted with water at a ratio of 1:1 (50%). Three solutions were prepared as controls: control solution 1, which consisted of an aqueous solution containing the same active ingredients—arbutin and aloesin—in the same concentration as the composition of Example 1, but not containing the phospholipids or formulated as liposomes, control solution 2, which was the same as control solution 1 and control solution 3, which consisted of a liposome dispersion analogous to Example 1, but without the active substances—arbutin and aloesin. The five formulations were applied to the forearm of four light-skinned test people (skin type II) twice daily (20 μL per application), in the morning and in the evening. The solutions were left on the skin for 30 minutes, then the application sites were exposed to light from a Philips HB311 UV solarium (UV-A light with a small amount of UV-B) for 25 minutes. Within 10–14 days, a de-pigmentation effect was visible to the naked eye in those areas treated with the composition according to the present invention. This effect was clearly visible with both concentrations of the composition tested. Among the areas treated with the control solutions, there was no effect visible to the naked eye within the test period. The de-pigmentation was visible to the naked eye for over 14 days after application of the active substances had been discontinued and then faded. No patchiness could be detected.

Example 3

In Vitro Enzyme Activity of Tyrosinase in the Presence of Arbutin and Aloesin An in vitro tyrosinase inhibition assay was carried out using a modification of the procedure described by Pomerantz (1993) J. Biol. Chem. 238:2351–2357. According to this method, the conversion of L-Dopa, a substrate of tyrosinase, into dopaquinone and then dopachrome is followed by monitoring absorption at 475 nm in a spectrophotometer. As the colored substance dopachrome absorbs light having a wavelength of 475 nm, a quantitative measurement of the time-related conversion and thus the activity of tyrosinase can be made.

All samples had a final volume of 1.5 mL. Each sample was prepared in a 50 mM potassium phosphate buffer which had been adjusted to pH 6.8, and stabilized by the addition of 10% DMSO. Tyrosinase (48 u, "u" represents the activity units of an enzyme, measured in mM substratum conversion per minute) was added to each sample. A double assessment was carried out for each inhibitor, using two different starting concentrations of L-Dopa: 0.4 mM and 0.2 mM. Controls were also run using the same concentrations of uninhibited tyrosinase to serve as the neutral value. In the control samples the volume of inhibitor was replaced with 50 mM potassium phosphate buffer. The time-related difference in absorption, and thus the conversion of L-Dopa, was followed for a period of two minutes.

The conversion kinetics of the tyrosinase was measured upon addition of the following concentrations of inhibitor: arbutin (0.9 mM); aloesin (0.0192 mM; 0.0385 mM and 0.0769 mM) and with the respective combination of both of the inhibitors. Enzyme inhibition was determined from the difference between the inhibited and the uninhibited kinetics. The results are set forth in Table 2. It is worth noting that the compositions examined in this example contain no liposomes, as the penetration ability and bio-availability are of no significance in an in vitro test. The purpose of these in vitro studies was to determine the efficacy of the inhibitors (arbutin and aloesin) individually and combinations thereof. As can be seen in Table 2, a more or less additive enzyme inhibitory effect was achieved at all concentrations measured.

TABLE 2

Summary of the Concentration of Inhibitor and % Inhibition of Tyrosinase

| Inhibitor | Concentration (mM) | % Inhibition Tyrosinase |
|---|---|---|
| arbutin | 0.9 | 29% |
| aloesin | 0.0192 | 20%, |
| aloesin | 0.0385 | 32% |
| aloesin | 0.0769 | 46% |
| arbutin | 0.9 | 53% |
| aloesin | 0.0192 | |
| arbutin | 0.9 | 61% |
| aloesin | 0.0385 | |
| arbutin | 0.9 | 73% |
| aloesin | 0.0769 | |

What is claimed is:

1. An aqueous composition comprising liposomes comprised of phospholipids, and at least one competitive inhibitor of an enzyme for the synthesis of melanin, in combination with at least one non-competitive inhibitor of an enzyme for the synthesis of melanin, wherein said enzyme is tyrosinase and at least one of said non-competitive inhibitors is selected from the group consisting of compounds having the following chemical structures:

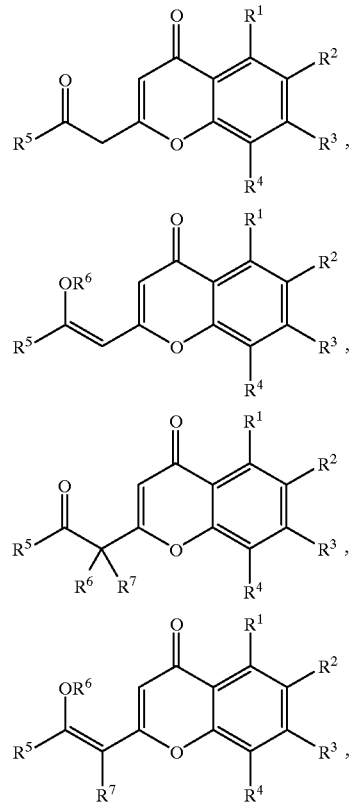

wherein $R^1$, $R^2$, $R^3$, $R^4$, $R^5$, $R^6$ and $R^7$ are independently selected from the group consisting of H, alkyl, alkoxy, acyl, acyloxy, acylamino and polyalcohols or derivatives thereof including sugar derivatives, wherein said alkyl, alkoxy, acyl, acyloxy, acylamino and polyalcohol groups and derivatives thereof can be saturated or unsaturated and have between 1 and 20 carbon atoms, and wherein at least one of said competitive inhibitors is arbutin.

2. The composition of claim 1, wherein said at least one of said non-competitive inhibitor is selected from the group consisting of compounds having the following chemical structure:

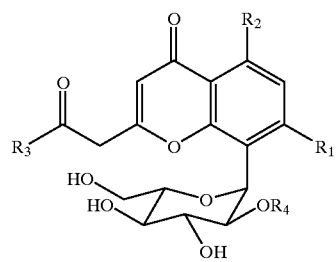

wherein $R_1$, $R_2$ and $R_3$ are independently selected from the group consisting of H, OH, alkyl groups having from 1 to 20 carbon atoms, alkoxy groups having from 1 to 20 carbon atoms, acyl groups having from 1 to 20 carbon atoms, acyloxy groups having from 1 to 20 carbon atoms, acylamino groups having from 1 to 20 carbon atoms, and polyalcohol groups, wherein each of said alkyl, alkoxy, acyl, acyloxy and acylamino groups may be saturated, unsaturated and substituted; and $R_4$ is selected from the group consisting of aromatic substituted carboxylic acids attached to the linking oxygen via the carboxyl carbon thereby forming the ester, wherein said carboxylic acids are selected from the consisting of phenylacetic acid, DOPA, tyrosine and cinnamic acid and its derivatives, ferulic acid and kojic acid.

3. The composition of claim 2, wherein said non-competitive inhibitor is octylaloesin.

4. The composition of claim 1, comprising a concentration of about 0.05 to 7.5 percent by weight of said competitive inhibitor, and a concentration of about 0.05 to 1.5 percent by weight of said non-competitive inhibitor, each based on the total weight of the composition.

5. The composition of claim 2, comprising a concentration of about 3.5 to 5.5 percent by weight of arbutin, and a concentration of about 0.75 to 1.25 percent by weight of aloesin or aloesin derivative, each based on the total weight of the composition.

6. The composition of claim 1, further comprising one or more alcohols in an amount of up to 20 percent by weight, based on the total weight of the composition.

7. The composition of claim 6 wherein said alcohols are selected from the group consisting of ethanol and i-propanol.

8. The composition of claim 1, comprising a concentration of about 5 to 20 percent by weight of phospholipids.

9. The composition according to claim 2, comprising a concentration of about 4 percent by weight of arbutin, a concentration of about 1 percent by weight of aloesin or a derivative thereof, a concentration of about 10 percent by weight of phospholipids and a concentration of about 16 percent by weight of an alcohol, each based on the total weight of the composition.

10. The composition of claim 1, further comprising one or more additional active substances for de-pigmentation.

11. The composition of claim 1, wherein said phospholipids are extracted from soya, and have a phosphatidyl choline content of at least 73 percent by weight, based on the total weight of phospholipids.

12. The composition of claim 1, wherein said phospholipids are hydrogenated, and have a phosphatidyl choline content of at least 73 percent by weight, based on the total weight of phospholipids.

13. The composition of claim 11, wherein said phospholipids have the following fatty acid composition: about 61 to 71 percent linoleic acid, about 3 to 7 percent of linolenic acid, about 6 to 13 percent of oleic acid, about 10 to 15 percent of palmitic acid and about 1.5 to 4 percent of stearic acid, each based on the total weight of the fatty acid residues.

14. The composition of claim 1, wherein the vesicle size of said liposomes is about 80 to 400 nm.

15. A method for the reversible de-pigmentation of the skin comprising, topically applying a composition comprising the composition of claim 1.

* * * * *

UNITED STATES PATENT AND TRADEMARK OFFICE
CERTIFICATE OF CORRECTION

PATENT NO. : 6,123,959
DATED : September 26, 2000
INVENTOR(S) : Kenneth Jones, Abeysinghe Padmapriya, Ernst E. Teichmüller and Gabriele Blume It is certified that error appears in the above-identified patent and that said Letters Patent is hereby corrected as shown below:

On the cover page, inventor Gabriele Blume's city of residence is Steinau a.d. Strasse.

On the cover page, assignee should read:
    Assignee:    Univera Pharmaceuticals, Inc., Broomfield, Colorado
                    ROVI GmbH, Schlüchtern, Germany Signed and Sealed this Fifteenth Day of May, 2001

*Attest:*

NICHOLAS P. GODICI

*Attesting Officer*      *Acting Director of the United States Patent and Trademark Office*

UNITED STATES PATENT AND TRADEMARK OFFICE
CERTIFICATE OF CORRECTION

PATENT NO. : 6,123,959
DATED : September 26, 2000
INVENTOR(S) : Kenneth Jones et al.

It is certified that error appears in the above-identified patent and that said Letters Patent is hereby corrected as shown below:

<u>Title page,</u>
Item [75], Inventors, Gariele Blume's city of residence is -- Steinau a.d. Strasse --.
Item [73], Assignee, should read:
-- [73]   Assignee:   Univera Pharmaceuticals, Inc., Broomfield, Colorado
                      ROVI GmbH, Schlüchtern, Germany --

Signed and Sealed this

Fifth Day of October, 2004

JON W. DUDAS
*Director of the United States Patent and Trademark Office*